United States Patent [19]

Pepe et al.

[11] Patent Number: 4,849,263

[45] Date of Patent: Jul. 18, 1989

[54] METHOD OF PRETREATMENT OF INORGANICS WITH NOVEL N-SILYL SUBSTITUTED 1-SILA-2-AZACYCLOALKANES

[75] Inventors: Enrico J. Pepe, Amawalk, N.Y.; Pedro M. Tarin, Juarez, Chihuahua, Mexico

[73] Assignee: Union Carbide Corporation, Danbury, Conn.

[21] Appl. No.: 68,567

[22] Filed: Jun. 30, 1987

[51] Int. Cl.$^4$ ............................................. B05D 3/04
[52] U.S. Cl. ................................... 427/336; 428/429; 528/33; 528/37; 427/387; 427/389.8
[58] Field of Search .................... 427/336, 389.8, 387; 428/429; 528/33, 37

[56] References Cited

U.S. PATENT DOCUMENTS

| | | | |
|---|---|---|---|
| 4,578,492 | 3/1986 | Pratt et al. | 556/407 |
| 4,582,887 | 4/1986 | Dominguez et al. | 528/48 |
| 4,584,393 | 4/1986 | Webb et al. | 556/407 |
| 4,607,090 | 8/1986 | Dominguez et al. | 528/48 |

OTHER PUBLICATIONS

Journal of Organic Chemistry, vol. 34, p. 3676 (1969).
Zhurual Obshchei Khimii, vol. 42, No. 4, pp. 858–862, reprinted as Journal Gen. Chemistry (USSR) vol. 42(4), pp. 848–852 (1972).

*Primary Examiner*—Melvyn I. Marquis
*Attorney, Agent, or Firm*—Eugene C. Trautlein

[57] ABSTRACT

This invention relates to a method of pretreatment of inorganics, such as fibers, with members of a class of N-silyl substituted 1-sila-2-azacyclopentane compounds and to a process for making composite materials therefrom. In a preferred embodiment of the instant invention, the pretreatment of fiberglass with 1,1-dimethoxy-2-(trimethoxysilyl)-1-sila-2-azacyclo-pentane is disclosed.

14 Claims, No Drawings

METHOD OF PRETREATMENT OF INORGANICS WITH NOVEL N-SILYL SUBSTITUTED 1-SILA-2-AZACYCLOALKANES

BACKGROUND OF THE INVENTION

1. Field of the Invention

The instant invention relates to a method of pretreatment of inorganic materials, such as glass, fibers with compounds selected from the class of N-silyl substituted 1-silyl-2-azacycloaklanes. The instant invention also relates to a process for making composite materials in which said pretreated inorganic materials are incorporated.

2. Prior Art

Various silane compounds have previously been employed as coupling agents for use in reinforced reaction injection molding (RRIM) technology. For instance, U.S. Pat. No. 4,582,887 discloses the use of chlorosilanes and isocyanate silanes as coupling agents in the practice of this technology. U.S. Pat. No. 4,607,090 discloses the use of epoxy silanes for the same function.

Zhurnal Obshchei Khimii, Volume 42, No. 4, pp. 858-862 has reported the possible formation of minor amounts of 1,1,1-triethoxy-N-[3-(triethoxysilyl)propyl]-silylamine during the hydrosilylation of allylamine. However, no mention of the cyclic derivatives was reported.

The Journal of Organic Chemistry Vol. 34, 3676 (1969) has reported the synthesis of the cyclic structure 1,1-diethoxy-2-(trimethylsilyl)-1-sila-2-azacyclopentane. This compound, however, lacks a hydroxyzable moiety and therefore would not perform satisfactorily to reinforce or couple in RRIM compositions due to trimethylsilylation of siliceous surfaces, reducing their reactivity with and/or wetting by typical RIM polymer matrices and also reducing their reactivity to subsequent treatments by conventional silane coupling agents. Therefore, subsequent applications of conventional coupling materials, such as 3-aminopropyltrimethoxysilane, to the glass fibers, will result in diminished bond strength, thereby making the use of 1,1-diethoxy-2-(trimethylsily)-1-sila-2-azacyclopentane undesirable in RRIM applications.

OBJECTS OF THE INVENTION

It is an object of the invention to provide a method of pretreatment of inorganic materials, such as glass fibers, with compounds selected from the class of N-silyl substituted 1-sila-2-azacycloalkanes compounds.

It is a further object of the present invention to provide a method of pretreatment of inorganic materials, such as glass fibers, with a compound, namely, 1,1-dimethoxy-2-(trimethoxysilyl)-1-sila-2-azacyclopentane.

It is yet another object of the present invention to provide a method of making various composite materials from said inorganic materials pretreated with the N-silyl substituted 1-sila-2-azacycloalkanes compounds.

SUMMARY OF THE INVENTION

The present invention provides a novel method of pretreatment of inorganic materials, such as glass fibers, through coating with at least one member of the class of certain hydrolyzable N-silyl substituted 1-sila-2-azacycloalkanes, followed by hydrolysis to its corresponding silanol derivative. This novel class of compounds is represented by the formula:

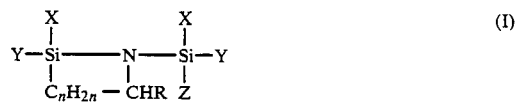

wherein Y and Z individually are selected from the group consisting of a hdyrogen atom, alkyl groups having from 1 to 4 carbon atoms, alkoxy groups having from 1 to 4 carbon atoms and dialkylamino groups having from 1 to 4 carbon atoms, X individually is selected from the group consisting of a hdyrogen atom, alkoxy groups having from 1 to 4 carbon atoms and dialkylamino groups having from 1 to 4 carbon atoms, R is selected from the group consisting of a hydrogen atom and an alkyl group having from 1 to 4 carbon atoms, and n is an integer having a value of from 2 to 4.

In a preferred embodiment of the present invention, there is provided a method for pretreatment of these inorganic materials through contact with and subsequent hydrolysis of 1,1-dimethoxy-2-(trimethoxysilyl)-1-sila-2-azacyclo-pentane represented by the formula:

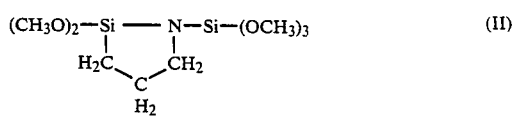

The present invention also provides a method for making composite materials through incorporation of inorganic materials pretreated with N-silyl substituted 1-sila-2-azacycloalkanes.

DETAILED DESCRIPTION OF THE INVENTION

The N-silyl substituted 1-sila-2-azacycloalkanes used in accordance with the instant invention and represented by the formula (I) above are produced through a catalyzed or uncatalyzed condensation reaction between an aminoalkyl silane and a substituted silane, such as an alkoxy silane, both of which are commerically available, followed by a thermally induced cyclization reaction.

In the case of the compound represented by Formula (II) used in a preferred embodiment of the present invention, the reaction sequence may be represented as set forth immediately below.

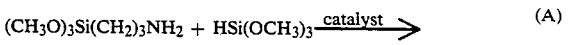

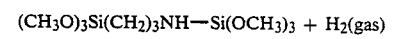

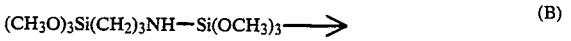

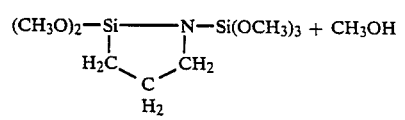

The starting materials used in Reaction (A) above are known materials produced by known processes.

Reaction (A) above is preferably conducted in the presence of a catalyst. Among those catalysts useful in the reaction are platinum, rhodium, palladium, and iridium.

Preferably, a platinum catalyst is employed in Reaction (A). The term platinum catalyst is used to define and encompass the platinum metal (supported or unsupported), platinum compounds and platinum complexes. Such catalysts are well known in the art as seen for example by U.S. Pat. Nos. 2,823,218, 2,851,473 and U.S. Pat. No. 3,410,886. Illustrative of the above catalysts are platinum, platinum-on-alumina; platinum-on-charcoal; chloroplatinic acid, platinum black; platinum-olefin; platinum-cycloalkane; bis(benzonitrile)-dichloroplatinum (II); and bis)phenyl-butyronitrile)-dichloroplatinum (II). Chloroplatinic acid is the preferred catalyst.

While only a catalytic amount of catalyst is necessary for the instant reaction, the amount of catalyst may vary over a wide range. Generally the catalyst is employed such that about 5 to about 1000 parts by weight of metal per million parts by weight of total reactants is employed, while the preferred range is from about 20 to about 500 parts by weight of metal per million parts by weight of total reactants.

Reaction temperatures for Reaction (A) may vary from about 50° C. to about 125° C. Preferably, reaction tempertures should range from about 80° C. to about 110° C. Most preferably, reaction temperatures should range from about 90° C. to about 100° C.

Reaction (A) is preferably carried out with agitation and at or near atmospheric pressure. The reaction is typically conducted in the presence of an inert solvent, such as toluene. Typically, the solvent should be present in amounts ranging from about 10 to about 90 wt. %. Preferably, the solvent is present in amounts ranging from about 20 to 80 wt. %, while, most preferably, it is present in amounts of between 30 and 70 wt. %. Reaction times, of course, depend upon other variables, such as reaction temperature and catalyst concentration. Typically, reaction times vary between about 30 minutes and 300 minutes.

Reaction (B) does not require the use of a catalyst. Reaction temperatures for Reaction (B) may vary from about 85° C. to about 145° C. Preferably,.reaction temperatures range from about 100° C. to about 130° C. Most preferably, reaction temperatures range from about 115° C. to about 125° C.

Reaction (B) is preferably carried out with agitation during reduced pressure distillation. Reaction times, of course, depend upon other variables, such as distillation temperature and pressure. Typically, reaction times vary between about 90 minutes and 180 minutes. The desired compounds are continuously recovered as formed and separated from the noncyclic precursor by conventional distillation techniques.

The above-described compounds are then contacted with various inorganic substrates, such as prior to incorporation of such substrates in composite materials, such as chopped or milled glass fibers in the polyurethane RRIM process. Articles manufactured through the RRIM process which employ such pretreated inorganic substrates exhibit increased strength. While not wishing to be bound by the following hypothesis, it is believed that, in the case of the inorganic substrate being glass fibers fibers, the increase in strength is attributable to an increase in surface silanol bonding sites available on the glass fibers after treatment with the above-described compounds. Therefore, subsequent application of conventional coupling agents results in an increased amount of coupling agent bound to the glass fibers. Alternatively, it is believed the above-described compounds may alter the glass fiber surface in some other way.

Polyurethane RRIM technology is well known as shown in U.S. Pat. Nos. 4,581,470; 4,585,850; 4,582,887; 4,549,007; 4,610,835; 4,601,936; and 4,607,090. Generally, it involves the reaction between a filler material, a polyol, an organic polyisocyanate, a coupling agent and a catalyst within a mold under pressure at a temperature selected to provide the desired reactivity, followed by removing (or de-molding) the molded product.

Filler materials useful in the manufacture of RRIM articles include glass fibers, flaked glass, wollastonite, mica or other mineral fillers.

The polyols useful in the practice of RRIM technology are well known. They include:

(a) alkylene oxide adducts of polyhydroxyalkanes;

(b) alkylene oxide adducts of nonreducing sugars and sugar derivatives;

(c) alkylene oxide adducts of phosphorus and polyphosphorus acids;

(d) alkylene oxide adducts of polyphenols;

(e) the polyols from natural oils such as castor oil, and the like.

Illustrative alkylene oxide adducts of polyhydroxyalkanes include, among others, the alkylene oxide addcts of ethylene glycol, propylene glycol, 1,3-dihydroxypropane, 1,3-dihydroxybutane, 1,4-dihydroxybutane, 1,4-, 1,5- and 1,6-dihydroxyhexane, 1,2-, 1,3- 1,4-, 1,6-, and 1,8-dihydroxyoctaine, 1,10-dihydroxydecane, glycerol, 1,2,4-trihydroxybutane, 1,2,6-trihydroxyhexane, 1,1,1-trimethylolethane, 1,1,1-trimethylolpropane, pentaerythritol, caprolactone, polycaprolactone, xylitol, arabitol, sorbitol, mannitol, and the like.

A further class of polyols which can be employed are the alkylene oxide adducts of the nonreducing sugars, wherein the alkylene oxides have from 2 to 4 carbon atoms. Among the nonreducing sugars and sugar derivatives contemplated are sucrose, alkyl glycosides such as methyl glucoside, ethyl glucoside, and the like, glycol glycosides such as ethylene glycol glucoside, propylene glycol glycoside, glycerol glucoside, 1,2,6-hexanetriol glucoside, and the like, as well as the alkylene oxide adducts of the alkyl glycosides as set forth in U.S. Pat. No. 3,073,788.

A still further useful class of polyols is the polyphenols, and preferably the alkylene oxide adducts thereof wherein the alkylene oxides have from 2 to 4 carbon atoms. Among the polypheols which are contemplated are, for example bisphenol A, bisphenol F, condensation products of phenol and formaldehyde, and novolac resins; condensation products of various phenolic compounds and acrolein, the simplest member of this class being 1,2,3-tris-(hydroxyphenyl) propane, condensation products of various phenolic compounds and glyoxal, glutaraldehyde, and other dialdehydes, the simplest member of this class being 1,1,2,2-tetrakis (hydroxyphenol) ethane, and the like.

The alkylene oxide adducts of phosphorus and polyphosphorus acids are another useful class of polyols. Ethylene oxide, 1,2-epoxypropane, the epoxybutanes, 3-chloro-1,2-epoxypropane, and the like are preferred alkylene oxids, Phosphoric acid, phosphorus acid, the polyphosphoric acids such as tripolyphosphoric acid, the polymetaphosphoric acids, and the like are desirable for use in this connection.

Indeed, any material having an active hydrogen as determined by the Zerewitinoff test may be utilized as the base polyol. For example, amine-terminated polyether polyols are known and may be utilized, if desired.

The polyols useful in RRIM applications also include the poly(oxypropylene) glycols, triols, and higher functionality polyols, and the like that are capped with ethylene or propylene oxide as dictated by the reactivity requirements of the particular polyurethane application. Generally, the nominal functionality of such polyols will be in the range of from about 3 to 4 or so. These polyols also include poly(oxypropylene-oxyethylene) polyols; however, desirably, the oxyethylene content should comprise less than 80 percent of the total and preferably less than 60 percent. The ethylene oxide, when used, can be incorporated in any fashion along the polymer chain. State another way, the ethylene oxide can be incorporated either as internal blocks, as terminal blocks, or may be randomly distributed along the polyol chain.

Polymer-polyols may also be employed in RRIM applications. These materials are well known in the art. The basic technology is disclosed in Stamberger U.S. Pat. No. Re. 28,715 and U.S. Pat. No. Re. 29,118. Generally, in order to produce a conventional polymer/polyol, an ethylenically unsaturated monomer is polymerized in situ in an appropriate polyol. The polymerization produces a stable dispersed polymer in the polyol. The polymer dispersion, known as a polymer-polyol, can be employed as a reactant in a number of reactions (e.g., polyurethane-forming reactions) to introduce into the resultant product, as an integral part thereof, both the polyol and the dispersed polymer.

More specifically, conventional polymer-polyols may be produced by the following steps which are known in the art:

(a) dispersing an ethylenically unsaturated monomer in a polyol, and (b) polymerizing said monomer in said polyol by free radical addition polymerization in the presence of a conventional free-radical catalyst to provide a stable dispersion of polymer-polyol.

Polymer-polyols may be produced by polymerizing the ethylenically unsaturated monomers in the selected polyol at a temperature of from about 40° C. to 150° C. in the presence of a catalytically effective amount of a conventional free radical catalyst known to be suitable for the polymerization of ethylenically unsaturated monomers. In batch processing, the monomers may be fed into the polyol over about three hours while maintaining the polyol at about 80°–130° C., and the reactants are then maintained about 110°–130° C. for an additional hour. In the preferred continuous operation, monomer and polyol are introduced at rates which give an average residence time of about 10 to about 80 minutes, while reaction temperature is maintained in the range of about 110° C. to about 130° C.

Among the polyols that can be employed for producing polymer-polyols are hydroxyl-terminated polyesters, polyhydroxyalkanes, polyphenols, polyoxyalkylene polyols, or the like and the corresponding mercapto derivatives, all of which are described in more detail above.

The monomers which may be used are the polymerizable monomers characterized in that they have at least one polymerizable ethylenically unsaturated group of the type, (C=C). The monomers can be used singly or in combination to produce homopolymer/polyol or copolymer/polyol reactive compositions.

These monomers are well known in the art and include the hydrocarbon monomers such as butadiene, isoprene, 1,4-pentadiene, 1,6-hexadiene, 1,7-octadiene, styrene, alpha-methylstyrene, para-methylstryene, 2,4-dimethylstyrene, ethylstyrene, isopropylstyrene, butylstyrene, phenylstyrene, cyclohexylstyrene, benzylstyrene and the like, substituted styrenes such as chlorostyrene, 2,5-dichlorostyrene, bromostyrene, fluorostyrene, trifluorormethylstyrene, iodostyrene, cyanostyrene, nitrostyrene, N,N-dimethylaminostyrene, acetoxystyrene, methyl-4-vinylbenzoate, phenoxystyrene, p-vinyl diphenyl sulfide, p-vinylphenyl phenyl oxide, and the like; the acrylic and substituted acrylic monomers such as acrylic acid, methacrylic acid, methylacrylate, hydroxypropyl acrylate, 2-hydroxyethyl acrylate, 2-hydroxyethyl methacrylate, methyl methacrylate, cyclohexyl methacrylate, benzyl methacrylate, isopropyl methacrylate, hydroxypropyl methacrylate, octyl methacrylate, methacrylnitrile, methyl alpha-chloroacrylate, ethyl alpha-ethoxyacrylate, methyl alpha-acetamidoacrylate, butyl acrylate, 2-ethylhexyl acrylate, phenyl acrylate, phenyl methacrylate, acrylonitrile, alpha-chloroacrylonitrile, substituted acrylamides including N,N-dimethylacrylamide, N,N-dibenzylacrylamide, and methacrylyl formamide, and the like; the vinyl esters, vinyl ethers, vinyl ketones, etc., such as vinyl acetate, vinyl chloroacetate, vinyl alcohol, vinyl butyrate, isopropenyl acetate, vinyl formate, vinyl acrylate, vinyl methacrylate, vinyl methoxy acetate, vinyl benzoate, vinyl iodide, vinyl toluene, vinyl naphthalene, vinyl chloride, vinyl bromide, vinyl fluoride, vinylidene bromide, 1-chloro-1-fluoroethylene, vinylidene fluoride, vinyl methyl ether, vinyl ethyl ether, vinyl propyl ethers, vinyl butyl ethers, vinyl 2-ethylhexyl ether, vinyl phenyl ether, vinyl 2-methoxyethyl ether, methoxybutadiene, vinyl 2-butoxyethyl ether, 2,4-dihydro-1,2-pyran, 2-butoxy-2'-vinyloxy diethyl ether, vinyl 2-ethylmercaptoethyl ether, vinyl methyl ketone, vinyl ethyl ketone, vinyl phenyl ketone, vinyl ethyl sulfide, vinyl ethyl sulfone, N-methyl-N-vinyl acetamide, N-vinylpyrrolidone, vinyl imidazole, divinyl sulfide, divinyl sulfoxide, divinyl sulfone, sodium vinyl sulfonate, methyl vinyl sulfonate, N-vinyl pyrrole, and the like; dimethyl fumarate, dimethyl maleate, maleic acid, crotonic acid, fumaric acid, itaconic acid, t-butylaminoethyl methacrylate, dimethylaminoethyl methacrylate, glycidyl acrylate, allyl alcohol, gylcol monoesters of itaconic acid, diglycol esters of itaconic acid, methyl monoester of itaconic acid, dichloro-butadiene, vinyl pyridine, and the like. Any of the known polymerizable monomers can be used and the compounds listed above the illustrative and not restrictive of the monomers suitable for use in this invention. Preferably, styrene, acrylonitrile and vinylidene chloride are the monomers used.

The organic polyisocyanates that are useful in producing polyurea or polyurethane-urea elastomers in accordance with this invention are organic compounds that contain at least two isocyanato groups. Such compounds are well-known in the art. Suitable organic polyisocyanates include the hydrocarbon diisocyanates (e.g., the alkylene diisocyanates and the arylene diisocyanates), as well as known triisocyanates and polymethylene poly (phenylene isocyanates). Examples of suitable polyisocyanates are 2,4-diisocyanatotoluene, 2,6-diisocyanatotoluene (TDI), methylene bis(4-cyclohexyl isocyanate), isophorone diisocyanate, 1,2-diisocyanatoethane, 1,3-diisocyanatopropane, 1,2-diisocyanatopropane, 1,4-diisocyanatobutane, 1,5-diisocyanatopentane, 1,6-diisocyanatohexane, bis(3-isocyanatopropyl)ether, bis(3-isocyanatopropyl) sulfide, 1,7-diisocyanatoheptane, 1,5-diisocyanato-2,2-dimethylpentane, 1,6-diisocyanato-3-methoxyhexane, 1,8-diisocyanatooctane, 1,5-diisocyanato-2,4-trimethylpentane, 1,9-diisocyanatononane, 1,10-diisocyanatopropyl) ether of 1,4-butylene glycol, 1,11-diisocyanatoundecane, 1,12-diisocyanatododecane bis-(isocyanatohexyl) sulfide, 1,4-diisocyanatobenzene, 3,5-diisocyanato-o-xylene, 4,6-diisocyanato-m-xylene, 2,6-diisocyanato-p-xylene, tetramethylxylylene diisocyanate, 2,4-diisocyanato-1-chlorobenzene, 2,4-diisocyanate-1-nitrobenzene, 2,5-diisocyanato-1-nitrobenzene, 4,4-diphenylmethylene diisocyanate (MDI) and derivatives thereof, 3,3-diphenyl-methylene diisocyanate, and polymethylene poly (phenyleneisocyanates) as described in the literature and in many patents, for examle, U.S. Pat. Nos. 2,683,730; 2,950,263; 3,012,008; 3,344,162 and 3,362,979, and mixtures thereof. Additional aromatic polyisocyanates includes p-phenylene diisocyanate, polymethylene polyphenylisocyanate, 2,6-toluene diisocyanate, dianisidine diisocyanate, bitolylene diisocyanate, naphthalene-1,4-diisocyanate, bis(4-isocyanatophenyl)methane, bis(3-methyl-3-isocyanatophenyl)methane, bis(3-methyl-4-isocyanatophenyl)methane, and 4,4'-diphenylpropane diisocyanate.

In particular, the most preferred aromatic polyisocyanate for use in polyurea elastomers is MDI (4,4'-diphenyl-methane diisocyanate) or its derivatives. Such derivatives include liquid forms as described in U.S. Pat. No. 3,394,164 and so called modified forms as described in U.S. Pat. No. 3,152,162. The liquid forms of MDI are preferred because pure MDI is a solid and can be difficult to use.

Preferably the amount of isocyanates used is the stoichiometric amount based on all the ingredients in the formulation or greater than the stoichiometric amount, where the stoichiometric amount of isocyanate is equal to the sum of the number of equivalents of chain-extender and N-(polyoxyalkyl)-N-(alkyl)amine.

Of course, the term oplyisocyanate also includes quasi-propolyers of polyisocyanates with active hydrogen containing materials.

The coupling agents useful in the practice of RRIM technology are also well known. Among those which are most widely employed are the epoxy silanes, chlorosilanes, aminosilanes and isocyanate silanes. Typical examples of these materials include the following:

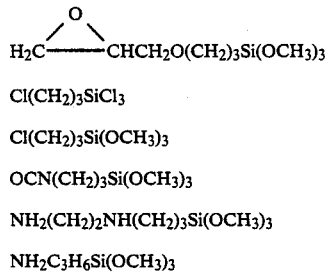

Cl(CH$_2$)$_3$SiCl$_3$

Cl(CH$_2$)$_3$Si(OCH$_3$)$_3$

OCN(CH$_2$)$_3$Si(OCH$_3$)$_3$

NH$_2$(CH$_2$)$_2$NH(CH$_2$)$_3$Si(OCH$_3$)$_3$

NH$_2$C$_3$H$_6$Si(OCH$_3$)$_3$

Catalysts such as tertiary amines or organic tin compounds or other polyurethane catalysts are used. The organic tin compound may suitably be a stannous or stannic compound such as a stannous salt of a carboxylic acid, a trialkyltin oxide, a dialkyltin dihalide, a dialkyltin oxide, etc., wherein the organic groups of the organic portion of the tin compound are hydrocarbon groups containing from 1 to 8 carbon atoms. For example, dibutyltin dilaurate, dibutyltin diacetate, diethyltin diacetate, dihexyltin diacetate, di-2-ethylexyltin oxide, dioctyltin dioxide, stannous octoate, stannous oleate, etc., or a mixture thereof, may be used.

Tertiary amine catalysts include trialkylamines (e.g., trimethylamine, triethylamine), heterocyclic amines, such as N-alkylmorpholines (e.g., N-methylmorpholine, N-ethylmorpholine, dimethyldiaminodiethylether, etc.) 1,4-dimethylpiperazine, triethylenediamine, etc., and aliphatic polyamines such as N,N,N'N'-tetramethyl-1,3-butanediamine.

Other conventional formulation ingredients may be employed as needed such as; for example, foam stabilizers, also known as silicon oils or emulsifiers. The foam stabilizers may be an organic silane or siloxane. For example, compounds may be used having the formula:

R-Si[O—(R$_2$SiO)$_n$—(oxyalkylene)$_m$R]$_3$ wherein R is an alkyl group containing from 1 to 4 carbon atoms; n is an integer of from 4 to 8; m is an integer of from 20 to 40; and the oxyalkylene groups are derived from propylene oxide and ethylene oxide, as shown in, for example, U.S. Pat. No. 3,194,773.

Also useful are chain extenders which include low molecular weight (i.e., less than about 400) polyfunctional compounds capable of reaction with an isocyanate. Typical examples include amino alcohols and glycols, such as 1,4-butanediol and ethylene glycol; aliphatic diamines; and aromatic diamines such as: 1-methyl-3,5-diethyl-2,4-diaminobenzene, 1-methyl-3,5-diethyl-2,6 diaminobenzene (both of these materials are also called diethyltoluene diamine or DETDA) tert-butyltoluene diamine, 1,3,5-triethyl-2,6 diaminobenzene, 3,5,3', 5'-tetraethyl-4,4" diaminodiphenylmethane and the like. Particularly preferred aromatic diamine chain extenders are 1-methyl-3,5-diethyl-2,4 diaminobenzene or a mixture of this compound with 1-methyl-3,5-diethyl-2,6 diaminobenzene. It is within the scope of this invention to include some aliphatic chain extender materials as described in U.S. Pat. Nos. 4,246,363 and 4,269,945.

Other forms of RRIM technology can obviously take advantage of the enhanced strengthening properties of glass fibers treated with the novel compounds of this invention. Included are polyurea RIM, polyamide RIM, epoxy RIM, and Rism Transfer Molding techniques. While the benefits of these compounds were discovered and illustrated in RIM technology, it is apparent to those skilled in the art of glass fibers reinforced composites that phenomena demonstrated in this way will also occur and be useful in processes that embody other ways of reacting, polymerizing, thermosetting or curing polymers in the presence of the glass fibers or other mineral surfaces which have been improved by treatment with the novel class of compounds. For instance, the present invention may be used in the production of composites based on polyesters, polyolefins, epoxies, phenolics, polysulfides and polyvinylchlorides. Furthermore, while the use of RRIM coupling agents, such as 3-aminopropyltriethoxysilane, has been disclosed, the use of other coupling agents in the formulation of non-RRIM composites is also within the scope of the present invention. For instance, the use of (CH$_3$O)$_3$ Si (CH$_2$)$_3$ SH as a coupling agent for polysulfide and polyvinyl-chloride-based composites while the use of

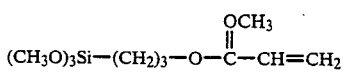

is similarly known in relation to polyester, polyolefin and peroxide-cured composites.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLE I

Into a 250 ml 3-necked flask equipped with thermometer, dropping funnel, magnetic stirring bar and electric heating mantle was charged 82.6 grams (0.46 moles) of $NH_2C_3H_6Si(OCH_3)_3$ and 122.2 grams (1.0 mole) of distilled $HSi(OCH_3)_3$ (having a boiling point of 82–85.5° C. at one atmosphere) added dropwise over ½ hour. A vigorous evolution of hydrogen was observed throughout with a slight exotherm. The reaction mixture was heated to reflux (100° C.) and hydrogen evolution stopped after about one hour. Distillation to a final temperature of 123° C. resulted in the recovery of about 77 grams of trimethoxysilane. The reaction appeared to be about 1/3 completed. The total distillate was re-charged and 0.21 gram of chlorophatinic acid was added dissolved in 4 milliliters of dimethoxyethane at room temperature such that the resultant concentration of platinum was about 400 parts per million (ppm) as platinum metal. The mixture was stirred in excess of 40 hours. Thereupon, heating for 8 additional hours produced a slow constant hydrogen evolution and the temperature of the reaction vessel rose from 100° C. to 125° C. An additional 20 grams of $HSi(OCH_3)_3$ were added and the mixture refluxed 1 hour to a 125° C. final temperature. Subsequent distillation recovered about 33 grams of predominantly $HSi(OCH_3)_3$ having a boiling point of about 85–105° C. About 175.8 grams of this crude reaction product was recovered.

The recovered reaction product was then distilled. Distillation data summarized below indicated continuous thermal breakdown of product. Distillation conditions are recorded as the distillation temperature in degrees Centigrade at a given pressure in millimeters of mercury (°C./mm.). Analysis by gas chromatography of fraction B of the distillation run showed 7 components with a 74 area % peak subsequently identified as 1,1-dimethoxy-2-(trimethoxysilyl)-1-sila-2-azacyclopentane, the structural formula of which is set forth above as Formula II.

| Fraction | Distillation Log °C./mm | gms. |
|---|---|---|
| A | 55°/0.1 | 64.5 |
| B | 55°/0.05 | 38.0 |
|   | 77°/0.013 |  |
| C | 90°/0.27 | 39.0 |
|   | 105°/0.03 |  |
| D | 125°/0.05 | 19.0 |
| Residue |  | 15.0 |

| Fraction | Distillation Log °C./mm | gms. |
|---|---|---|
| Losses |  | 3.0 |

Use $^{13}C$ and $^{29}Si$ nuclear magnetic resonance (NMR) apparatus confirmed that the predominant component in Fraction B was the cyclic compound of this invention having the Formula (II):

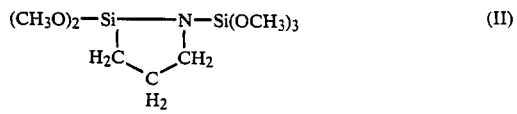

Chemical Ionization Mass Spectrometry with ammonia as the reagent gas was also used to confirm the molecular weight of this compound and identify minor impurities present in the distilled product. The structures of fine impurities are set forth below.

| Proposed Structures |
|---|
| $Si(OMe)_4$ |
| $NH_2(CH_2)_3Si(OMe)_3$ |
| $NH(CH_2)_3Si(OMe)_2$ |
| $(MeO)_3Si(CH_2)_3NHSi(OMe)_3$ |
| $(MeO)_3Si(CH_2)_3NHSiH(OMe)_2$ |

EXAMPLE 2

Bare glass fibers (1/16" milled) were sieve-fractionated to an average aspect ratio (α) of 13. Average aspect ratio is defined as the length to diameter ratio of the average fiber. This glass fiber aspect ratio distribution was prepared by placing about 60 grams of the milled glass fibers in a 105-micron sieve and shaking it onto a 75-micron sieve with the aid of a ROTAP® shaking unit for one minute. The fibers which passed through the 75-micron sieve were collected. This process was repeated several times. After about 60 grams of the fibers were collected, they were placed in the 105-micron sieve and re-shaken for one minute. Fibers that remained on the 105-micron sieve had a Gaussian-like distribution slightly skewed to the high fiber aspect ratio side. The distribution had an average aspect ratio of 13 and an estimated deviation of ±20%. The fiber aspect ratio distribution was quantitively determined using polarized light.

A two step treatment procedure was then employed to treat the fibers for their subsequent use in a RRIM composition. This technique involved application of a non-aqueous slurry of the claimed compound produced in Example I above, followed by a step wherein the glass surface bound silane ester groups and remaining silazane components of the claimed compound were hydrolyzed to their silanol derivatives through the addition of an aqueous solution of 3-aminopropyltriethoxysilane. Aminopropylsilane esters are coupling agents routinely empllyed, as aqueous solutions, in the preparation of RRIM compositions.

About 330 grams of bare glass fibers having an aspect ratio of about 13, were pre-conditioned through exposure to a dry nitrogen atmosphere for 24 hours. They were then added to a 1.8 wt. % anhydrous (4 ppm water) dimethoxy ethane (DME) solution of the compound produced in Example I, which is hereinafter referred to as Compound Q (15 grs. of Compound Q /800 grs. DME) in a beaker. The resulting slurry was agitated for an hour using a magnetic Teflon-coated bar and a magnetic stirred set at "medium" speed. The preparation of the Compound Q/DME solution, as well as its application to the glass fibers, were carefully carried out inside a glove box with a dry nitrogen atmosphere. Further, the glove box was thoroughly purged with dry nitrogen overnight, to reduce moisture contamination of the Compound Q/DME glass slurry.

The slurry was filtered using a stainless steel pressure filter. The fiber cake, at the bottom of the pressure filter, was pressure-rinsed twice with DME to remove any residual Compound Q. The rinsed fiber cake (still inside the steel container) was nitrogen dried at about 20 psi for about 30 minutes. At this point, the semi-dry fiber cake was handled outside of the glove box and was then put into a beaker containing 2.4 grams of $NH_2(CH_2)_3Si(OC_2H_5)_3$ dissolved in 800 grams of distilled water.

Glass fiber (35 wt. %) RRIM composites of both the treated fiber and a non-treated fiber were prepared using a Mini-RIM machine. The composition of the RRIM composite is set forth immediately below.

| Compound | Weight (grams) |
| --- | --- |
| polypropylene glycol polyol | 100.0 |
| methylene-diphenyl diisocyanate | 98.6 |
| dibutyltin dilaurate | 0.075 |
| 1/16 inch glass treated fibers | 106.6 |

Three-point, notch-bend specimens were tested at a strain rate of 200 in/min. and analysis of their respective fracture surfaces was done according to ASTM 638–67 and recommendations by Srawley, J.E. and Brown, Jr., W.F. "Fracture Testing Methods", Fracture Toughness Testing and its Applications, p. 133, ASTM (1965).

A RRIM composite was then also prepared as described above with the exception that the glass fibers employed were not treated with a claimed composition before application of $NH_2(CH_2)_3Si(OC_2H_5)_3$.

The mechanical performance of glass RRIM composites prepared with the use of compounds of the instant invention showed superior bonding performance. The fracture surface morphology shows embedded, well bonded, broken fibers. Further, the polymer is observed to be tenaciously adhered to the fibers. The fracture energies of the treated fiber RRIM composites were about $24 \pm 1$ inch-pounds/inch$^2$ while the fracture energies of the untreated fiber RRIM composities were about $19 \pm 1$ inch-pounds/inch$^2$.

What is claimed is:

1. A process comprising:
    (a) coating an inorganic material with a hydrolyzable. N-silyl substituted 1-sila-2-azacycloalkane of the formula:

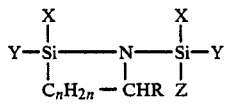

wherein Y and Z individually are selected from the group consisting of a hydrogen atom, alkyl groups having from 1 to 4 carbon atoms, alkoxy groups having from 1 to 4 carbon atoms and dialkylamino groups having from 1 to 4 carbon atoms, X is individually selected from the group consisting of a hydrogen atom, alkoxy groups having from 1 to 4 carbon atoms and dialkylamino groups having from 1 to 4 carbon atoms, R is selected from the group consisting of a hydrogen atom and an alkyl group having from 1 to 4 carbon atoms, and n is an integer having a value of from 2 to 4, and
    (b) hydrolyzing the said N-silyl substituted 1-sila-2azacycloalkane.

2. The process of claim 1 wherein the N-silyl substituted 1-sila-2-azacycloalkane is hydrolyzed by contacting the said coated inorganic material with an aqueous solution of 3-aminopropyltriethoxy silane.

3. The process of claim 1 wherein Y and Z of the N-silyl substituted 1-silyl-2-azacycloalkane are individually selected from the group consisting of a hydrogen atom, alkyl groups having from 1 to 2 carbon atoms, alkoxy groups having from 1 to 2 carbon atoms and dialkylamino groups having from 1 to 2 carbon atoms, and X individually is selected from the group consisting of a hydrogen atom, alkoxy groups having from 1 to 2 carbon atoms and dialkylamino groups having from 1 to 2 carbon atoms.

4. The process of claim 1 wherein X, Y and Z individually are alkoxy groups having from 1 to 2 carbon atoms.

5. The process of claim 1 wherein X, Y and Z are each individually dialkylamine groups having from 1 to 2 carbon atoms.

6. The process of claim 1 wherein the N-silyl substituted 1-sila-2-azacycloalkane is of the formula

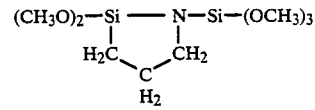

7. The process of claim 1 wherein the inorganic material is glass fibers.

8. A process for the preparation of composite materials comprising:
    (a) coating an inorganic material with a hydrolyzable, N-silyl substituted 1-sila-2-azacycloalkane of the formula:

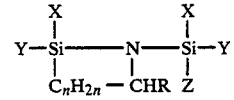

wherein Y and Z individually are selected from the group consisting of a hydrogen atom, alkyl groups having from 1 to 4 carbon atoms, alkoxy groups having from 1 to 4 carbon atoms and dialkylamino groups having from 1 to 4 carbon atoms, X is individually selected from the group consisting of a hydrogen atom, alkoxy groups having from 1 to 4 carbon atoms and dialkylamino groups having from 1 to 4 carbon atoms, R is selected from the group consisting of a hydrogen atom and an alkyl group having from 1 to 4 carbon atoms;
    (b) hydrolyzing the N-silyl substituted 1-sila-2-azacycloalkane of said inorganic material;
    (c) mixing the said inorganic material with at least one coupling agent selected from the group consisting of epoxy silanes, chlorosilanes, aminosilanes and isocyanate silanes; and (d) incorporating the resultant mixture into the matrix of a composite to be used in the production of shaped articles by a reaction injection molding operation.

9. The process of claim 8 wherein the N-silyl substituted 1-sila-2-azacycloalkane is hydrolyzed by contacting the said coated inorganic material with an aqeuous solution of 3-aminopropyltriethoxy silane.

10. The process of claim 8 wherein Y and Z of the N-silyl substituted 1-sila-2-azacycloalkane are individually selected from the group consisting of a hydrogen atom, alkyl groups having from 1 to 2 carbon atoms, alkoxy groups having from 1 to 2 carbon atoms and dialkylamino groups having from 1 to 2 carbon atoms, and X individually is selected from the group consisting of a hydrogen atom, alkoxy groups having from 1 to 2 carbon atoms and dialkylamino groups having from 1 to 2 carbon atoms.

11. The process of claim 8 wherein X, Y and Z individually are alkoxy groups having from 1 to 2 carbon atoms.

12. The process of claim 8 wherein X, Y and Z are each individually dialkylamino groups having from 1 to 2 carbon atoms.

13. The process of claim 8 wherein the N-silyl substituted 1-sila-2-azacycloalkane is of the formula

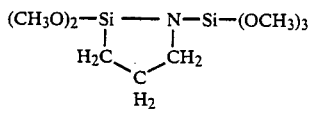

14. The process of claim 8 wherein the inorganic material is glass fibers.

* * * * *